United States Patent [19]
Toh

[11] Patent Number: 6,055,055
[45] Date of Patent: Apr. 25, 2000

[54] CROSS OPTICAL AXIS INSPECTION SYSTEM FOR INTEGRATED CIRCUITS

[75] Inventor: Peng Seng Toh, Parc Oasis, Singapore

[73] Assignee: Hewlett-Packard Company, Palo Alto, Calif.

[21] Appl. No.: 09/012,294

[22] Filed: Jan. 23, 1998

[51] Int. Cl.[7] ............................ G01B 11/24; G01N 21/00; G01N 21/86
[52] U.S. Cl. ...................... 356/376; 356/394; 356/237.2; 250/559.46
[58] Field of Search ................................ 356/237.4, 394, 356/376, 237.5, 237.2, 375; 250/559.46, 559.48, 559.49; 348/126

[56] References Cited

U.S. PATENT DOCUMENTS

| | | |
|---|---|---|
| 4,686,565 | 8/1987 | Ando . |
| 5,140,643 | 8/1992 | Izumi et al. ................................ 382/8 |
| 5,276,546 | 1/1994 | Palm et al. ............................. 359/202 |
| 5,563,703 | 10/1996 | Lebeau et al. .......................... 356/237 |

FOREIGN PATENT DOCUMENTS 3-210410  9/1991  Japan ..................................... 356/237

Primary Examiner—Samuel A. Turner
Assistant Examiner—Zandra V. Smith

[57] ABSTRACT

A method and an apparatus for the measurement and inspection of integrated circuit. Such an apparatus includes a camera for sensing an image of the integrated circuit (IC), an oblique light source, and a reflector. The camera has an optical axis passing through the IC normal to the plane of the IC. The oblique light source radiates light on the IC obliquely to the plane of the IC such that at least a portion of the oblique light source is positioned on one side of the optical axis. The reflector is positioned on the opposite side of the optical axis relative the portion of the oblique light source for reflecting light that crosses the optical axis from the oblique light source to the camera, such that at least a portion of the IC interposes between the portion of the oblique light source and the reflector. As a result, the shape of that portion of the IC is imaged on the camera by back-lighting. The leads on the IC can be inspected in this manner.

17 Claims, 12 Drawing Sheets

CROSS OPTICAL AXIS INSPECTION SYSTEM FOR INTEGRATED CIRCUITS

This invention relates generally to an inspection system by optical means and more specifically to an optical inspection system for inspecting integrated circuits by imaging.

BACKGROUND

The inspection of leads of Integrated Circuit (IC) packages are extremely important to the electronics industries. IC packages such as Quad Flat Pack (QFP), Plastic Leadless Chip Carrier (PLCC), Small Outline IC (SOIC), Small Outline J-Lead (SOJ), DPAK, Small Outline Transistor (SOT), and their derivatives having leads protruding out from the IC package body. These leads are the means for connecting the internal circuits to the outside world. The integrity of these leads is crucial to provide good electrical connectivity and therefore useful application of the IC.

An Integrated Circuit (IC) package typically has a square or rectangular plastic package moulded over the IC circuitry commonly known as the "die". The size of the package may range from 4×4 mm square to 32×32 mm square. Extending from the plastic package are leads that provide electrical connectivity from the die inside the IC package to the printed circuit boards (PCB). It is important for the IC package and the leads to possess accurate and consistent mechanical dimensions because of the use of highly automated PCB assembly machine to place and solder the ICs onto the PCB. Damaged, twisted, or out-of-place leads will likely lead to improper assembling and malfunction in the PCB assembly. In particular, for high lead count IC such as the Quad Flat Pack (QFP), which has leads on all four sides of the package, the mechanical requirements are even more stringent. There are several requirements of the leads and categories of defects that have to be measured include coplanarity, lead pitch, terminal dimension, standoff, and others. Lead defects include bent leads, solder plating defects, swept leads, burr, and the like.

Several techniques and systems that include special optical and lighting arrangements for the direct and indirect viewing of leads of IC packages are available on the market. There are two major categories of IC lead inspection and measurement systems. One category uses laser-scanning approach. The other commonly used techniques include shadow casting and back illuminating the lead profiles onto imaging planes. As an example, some method uses lasers to scan the leads of an IC from the top. Another uses a back illuminated system with image doubler that increases the resolution of the image. Yet another method uses a lead inspection system to locate the leads with reference to a reference plate on which the device is mounted and a real-time reference which is used to provide a known correlation between the image pixels and linear measurement One IC inspection system includes a displacement sensor in which the upward and downward coplanarity error of each lead is measured from a level change in the output signal of the sensor. Another system determines a position of at least one lead of an electronic component using shadow casting techniques.

However, various problems exist with these prior inspection techniques. In the case of laser scanning technique, the top surface instead of the bottom surface of a lead is measured. This presents a problem because the bottom surface and geometry of a lead is more important than the top surface, particularly in relation to the electrical connectivity of the leads. The thickness of the leads will vary from lead to lead as a result of the solder plating thickness. As a consequence, measuring the top surface of the leads is not equivalent to measuring the bottom surface. This is especially true in high precision measurement in the range of several micrometers. In addition, laser-scanning techniques cannot detect burrs on lead tips, which commonly occur as a result of the trim and form process in the manufacture of IC leads. The existence of burrs on lead tips is another important factor that influences the electrical connectivity of an IC package to PCB. Therefore, there is a need for methods and systems for reliable inspection of ICs, especially for a method and methods and systems that can reliably inspect the bottom surface of the IC leads.

SUMMARY OF THE PRESENT INVENTION

In one aspect, the present invention provides an improved inspection system that is especially suited for inspecting integrated circuits and which ameliorates the above problems. An embodiment of the apparatus for inspecting planar objects (e.g., an IC) includes a camera for sensing an image of the planar object (e.g., IC), an oblique light source, and a reflector. The camera has an optical axis passing through the planar object normal to the plane of the object. The oblique light source radiates light on the planar object obliquely to the plane of the IC such that at least a portion of the oblique light source is positioned on one side of the optical axis. The reflector is positioned on the opposite side of the optical axis relative the portion of the oblique light source for reflecting light that crosses the optical axis from the oblique light source to the camera. The portion of the light source, the planar object, and the reflector are arranged such that at least a portion of the planar object interposes between the portion of the oblique light source and the reflector. As a result, the shape of that portion of the planar object is imaged on the camera by back-lighting. In this manner, the leads on the IC can be inspected.

In one embodiment, the apparatus of the present invention has an inspection datum having an upper and a lower surface and including a viewing window extending between said upper and lower surfaces; and a transport operable to move an object above the inspection datum across the viewing window. The object (e.g., IC) can be inspected by a viewer below the window as the object is in motion above and across the window. This is practicable because in this embodiment the object is not in contact with any object other than the pick up head of the transport that picks up the object, which in the case of an IC contacts only the top surface of the IC body. In an embodiment, the image obtained by the viewer includes a plurality of image parts, with each image part being of a portion of the object. In such as case, the image parts can be obtained from different optical paths obtained by the use of a plurality of reflectors each reflect an image part The image parts can be all directed into the same viewer, e.g., a charge coupled device (CCD). The inspection system of the present invention is ideally suited to inspecting integrated circuits leads. Preferably the reflective means is adapted to obtain images of the respective sets of leads of the integrated circuit. The inspection system is suitable for all parts of leads such as gull-wing, j-bend and straight leads. Inspection can also be carried out on many types of packages such as thin QFP and very thin QFP or SOIC.

An advantage of a preferred embodiment of the present invention is that the measurement of the leads can be carried out while the object (e.g., IC) is on the move and need not be stopped. A further advantage is that the object can be inspected without having to come into contact with any object such as a pedestal for inspection and therefore eliminates any possibility of lead damage due to contact with another object The ability to inspect the integrated circuit package while it is moving reduces inspection time. Since the integrated circuit package does not need to come into contact with any object such as a pedestal during inspection, potential lead damages are totally eliminated.

Furthermore, the bottom side of the IC and thus the bottom side of the leads can be viewed and inspected. The use of back-light to illumine the object (e.g., including IC leads) for inspection increases the stability and repeatability of the inspection results. True three-dimension (3D) lead geometry such as coplanarity, terminal dimension, pitch and other parameters can be measured.

DESCRIPTIONS OF THE ACCOMPANIED DRAWINGS

For clarity, preferred embodiments of the invention are described with reference to the following illustrative figures. In the figures, like numerals refer to like features in the several views.

PREFERRED EMBODIMENTS OF THE INVENTION

In one embodiment, the inspection system of the present invention provides a technique for inspecting the bottom portion of the side edges of the object and preferably without contacting the bottom parts of the object. Furthermore, an embodiment enables inspecting the inspection of the object while the object is in motion using a using a real time reference plane. The reference plane is built into the inspection system and is imaged together with the IC under inspection.

Figure 1:
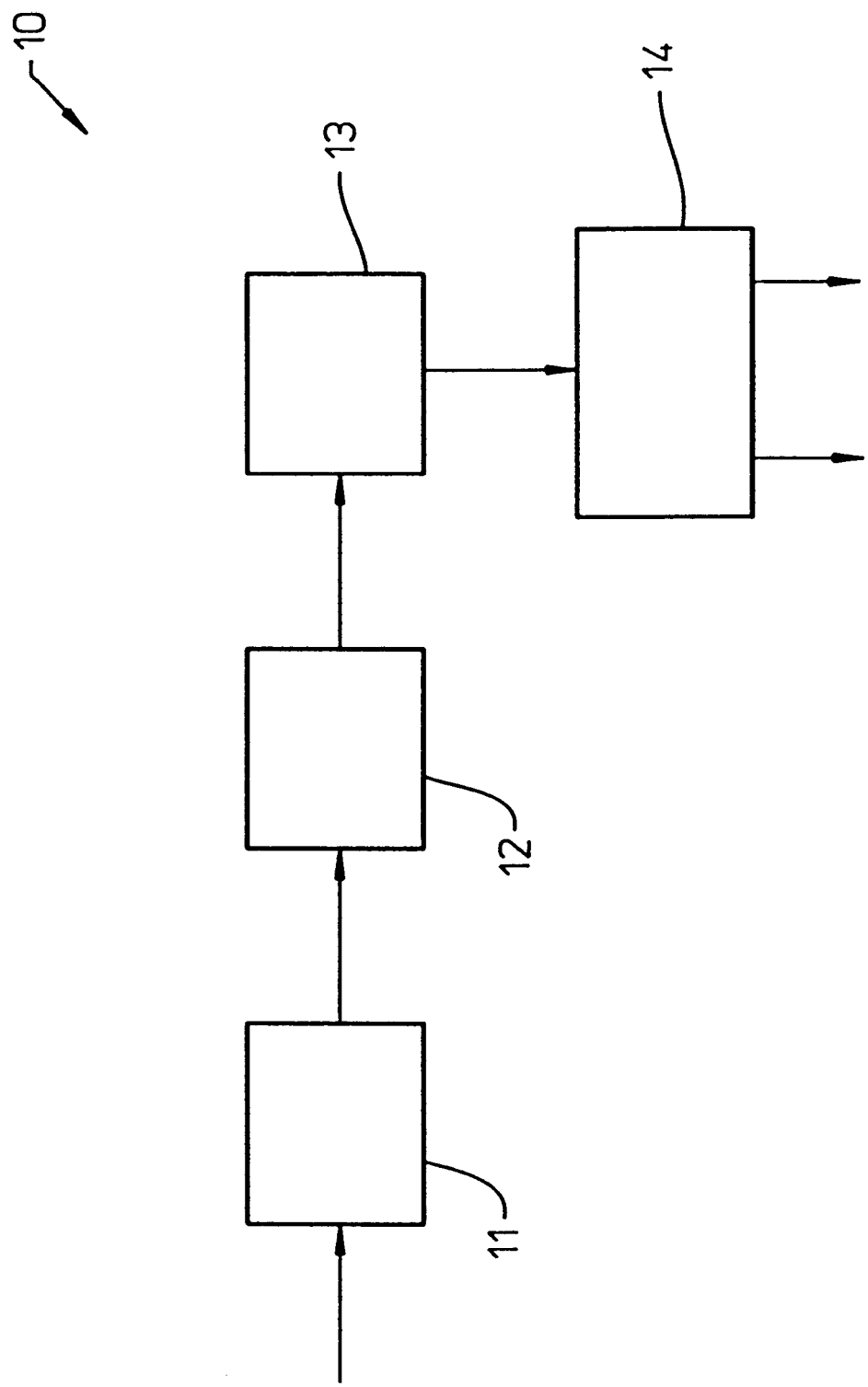
FIG. 1 is a block diagram of an inspection system for integrated circuits according to an embodiment of the invention.

FIG. 1 illustrates in block diagram an embodiment of an apparatus for inspecting three-dimensional objects. For convenience and clarity, hereinafter, the description will refer to an embodiment for inspecting three-dimension IC leads, although it is to be understood that the apparatus can be used for inspecting other objects, especially side edges of planar objects. The inspection system 10 includes four modules, namely the viewing optical module 11, the image acquisition module 12, the central processing module 13, and the control module 14.

Figure 2A:
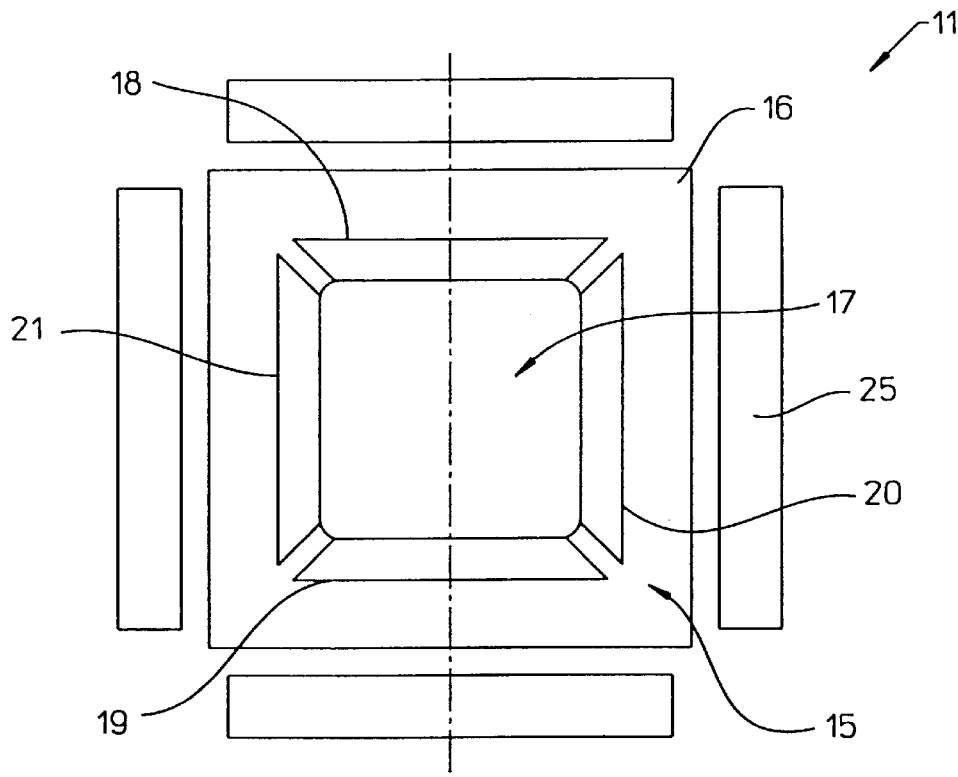
FIGS. 2a and 2b are a plan schematic view and a cross-sectional schematic elevation respectively of a first embodiment of the viewing optical module of the inspection system of FIG. 1.
Figure 2B:
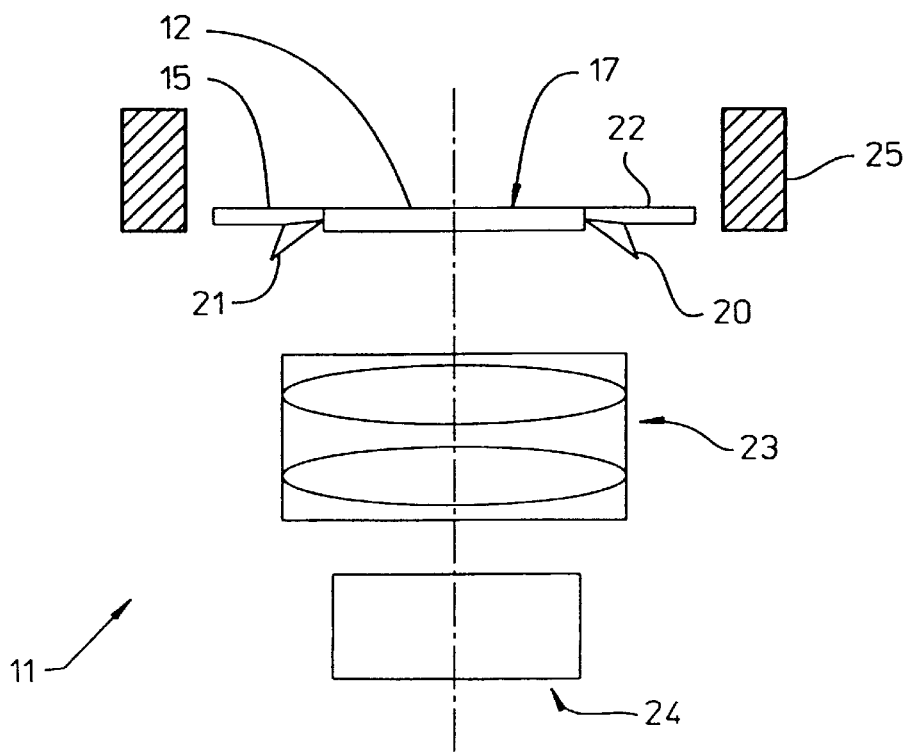

As shown in FIG. 2a, which shows a schematic bottom plan view, and FIG. 2b, which shows a schematic side view, the viewing optical module 11 includes an inspection datum 15 that has a sufficiently flat surface. The inspection datum 15 includes a frame 16 having an opening in its centre. The central opening in the inspection datum 15 is referred to as the viewing window 17. The viewing window 17 is an optically clear aperture allowing light of the desired wavelength to pass through. The size of the viewing window 17 is also adapted to be bigger than the size of the footprint of the IC 100 (not shown in FIG. 2 but shown in FIG. 3 and FIG. 4), which the system is arranged to inspect. The module 11 further includes reflectors 18, 19, 20 and 21 attached to the frame 16 just below the upper surfaces 22 of the datum 15. These reflectors 18, 19, 20, 21 are generally made up of either mirrors or prisms attached to the frame 16 adjacent the four sides of the viewing window 17.

The optical module 11 of the embodiment shown in FIG. 1 further includes a lens or len system 23 and video camera 24 and each of the reflectors 18, 19, 20, 21 reflects the image above the viewing window 17 into the lens 23 and further into the video camera 24. The lens 23 has telecentric property such that it is sufficiently tolerant to reasonable object distance variations. The video camera 24 is typically a Charged Coupled Device (CCD) camera which has a photo-sensitive array. The field of view of the video camera 24 encompasses the entire viewing window 17 and the four reflectors 18, 19, 20, 21.

The optical module 11 further includes uniformly illuminating light source 25, which can have parts, which are positioned around the viewing window 17. These uniformly illuminating light source parts 25 are used for back-lighting the IC 100. Back-lighting is an illumination technique that light up an object silhouette for which dimensional measurement can be effectively carried out In using back lighting technique, the object (i.e., the IC) to be measured is positioned between the viewer (camera) and the light source.

Figure 3:
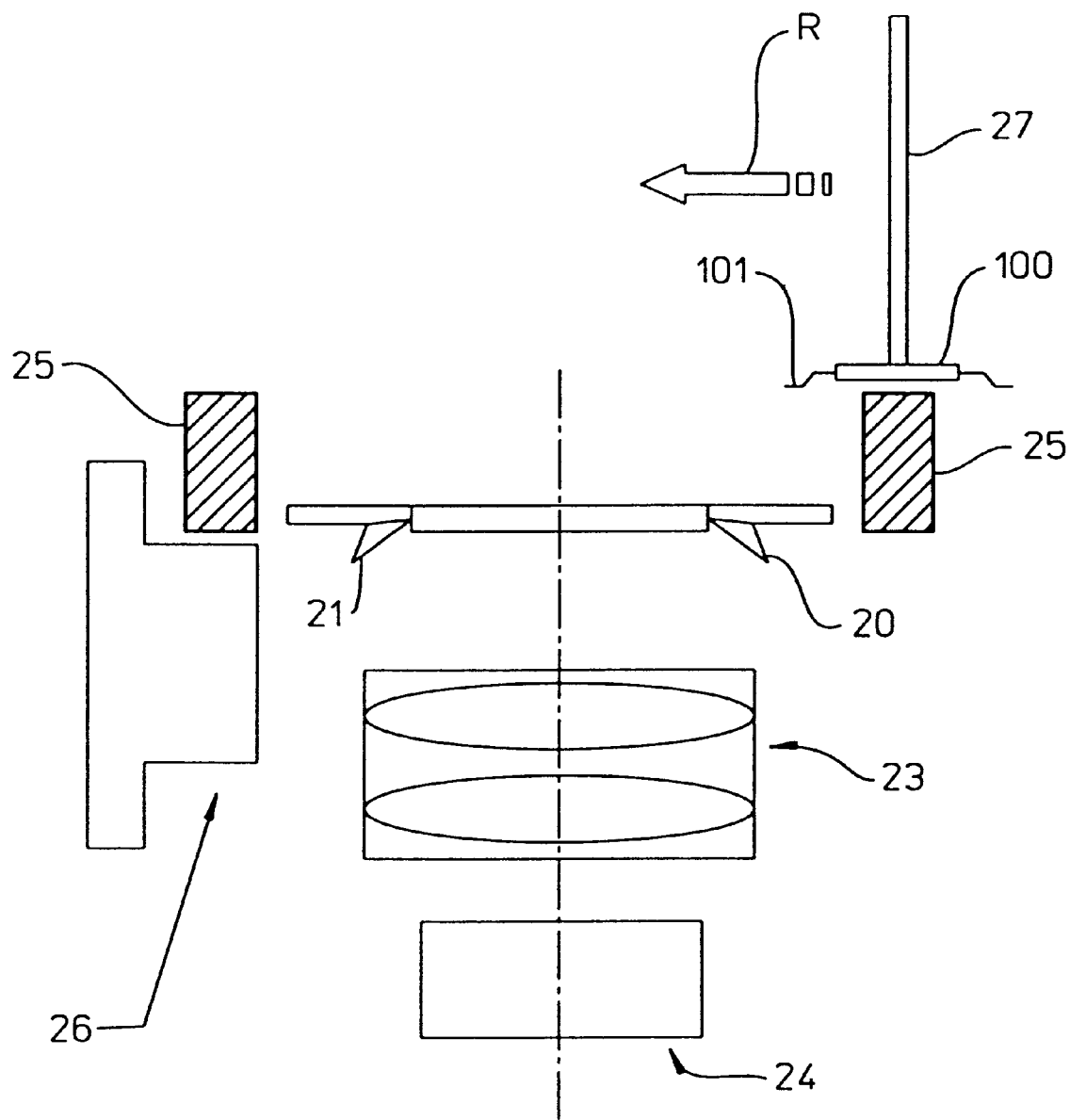
FIG. 3 is a schematic view of the optical module of FIGS. 2a and 2b illustrating the transporting of an IC across the module.

The uniform light source 25 can be either mounted onto the inspection datum 15 or onto a movable platform 26 (as shown in FIG. 3) surrounding the inspection datum. When the uniform light source 15 is mounted onto a movable platform 26, it is possible to lower the uniform light source 25 below the inspection datum 15 surface so that the inspection datum is clear of any object that may cause obstruction. In this way, the uniform light source 25 can be moved into place to illuminate the IC for imaging when the IC is proximate to the viewing window 17 (as in FIG. 4). The uniform light source 25 can be moved out of the way to allow the IC to be move into or out of the viewing optical module before and after imaging.

Figure 4A:
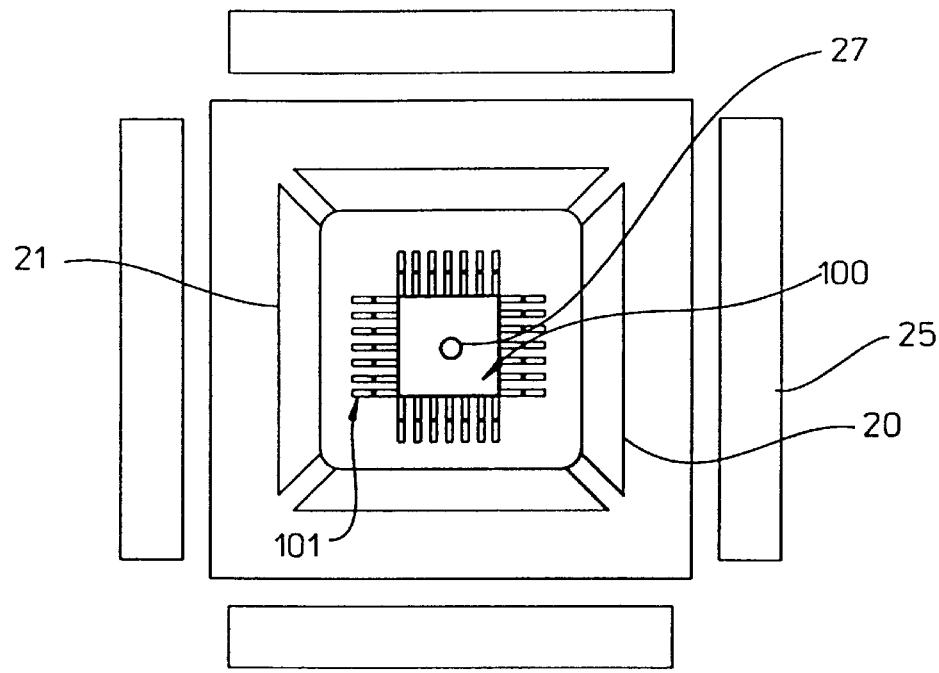
FIGS. 4a and 4b illustrate the viewing optical module with the IC in position.
Figure 4B:
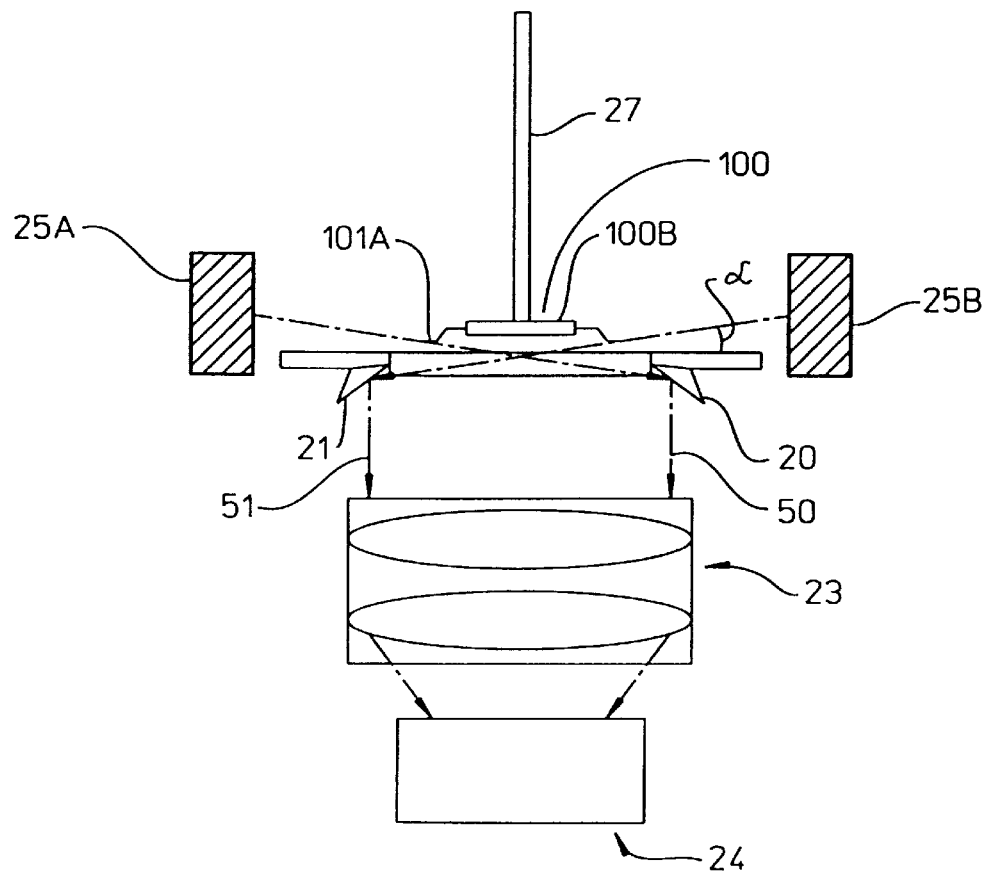

FIG. 3 and FIG. 4 show embodiments illustrating how an IC can be transported for inspection. As shown in FIGS. 3, 4a and 4b, an IC 100 to be inspected is picked up from the top by means of a pickup head 27 such as a suction cup. Such suction heads and suction cups are known in the art and commonly used in the IC industry. The pickup head 27 transports the IC over the viewing window 17. The bottom side of the IC 100 remains clear for inspection without any obstruction. The IC 100 is aligned in parallel to the upper surface 22 of the inspection datum 15 with seating plane of the IC 100 largely parallel to this surface 22. A small spacing is maintained between the inspection datum 15 and the seating plane of the IC 100. When the IC 100 is transported across the viewing window 17, no vertical movement is required to lower the IC 100 into the viewing window 17. When the IC 100 is at the appropriate location above the viewing window 17, the uniform light source 25 is moved up by the platform 26 to its active position to provide back light for the video camera 24 to acquire the image of the IC 100. After the image is acquired, the uniform light source 25 is moved downward to its inactive position to provide a clear passage for the IC 100 to be transported out of the inspection datum 15. Alternatively, the light source 25 can be attached to the pickup head 27 and hence move together with the pickup head 27.

As best illustrated in FIG. 4b, when the IC is moved to the location of the viewing window 17, the IC 100 is located between the uniformly illuminating light source 25 and the reflector 18, 19, 20, 21. This is a back-lighting technique as the reflector obtains an image of the IC 100 and its leads 101 in silhouette (e.g., see FIG. 8). The video camera 24 hence images the silhouettes of the IC 100 and its leads 101 through the reflector 18, 19, 20, 21 and the lens 23.

Figure 5:
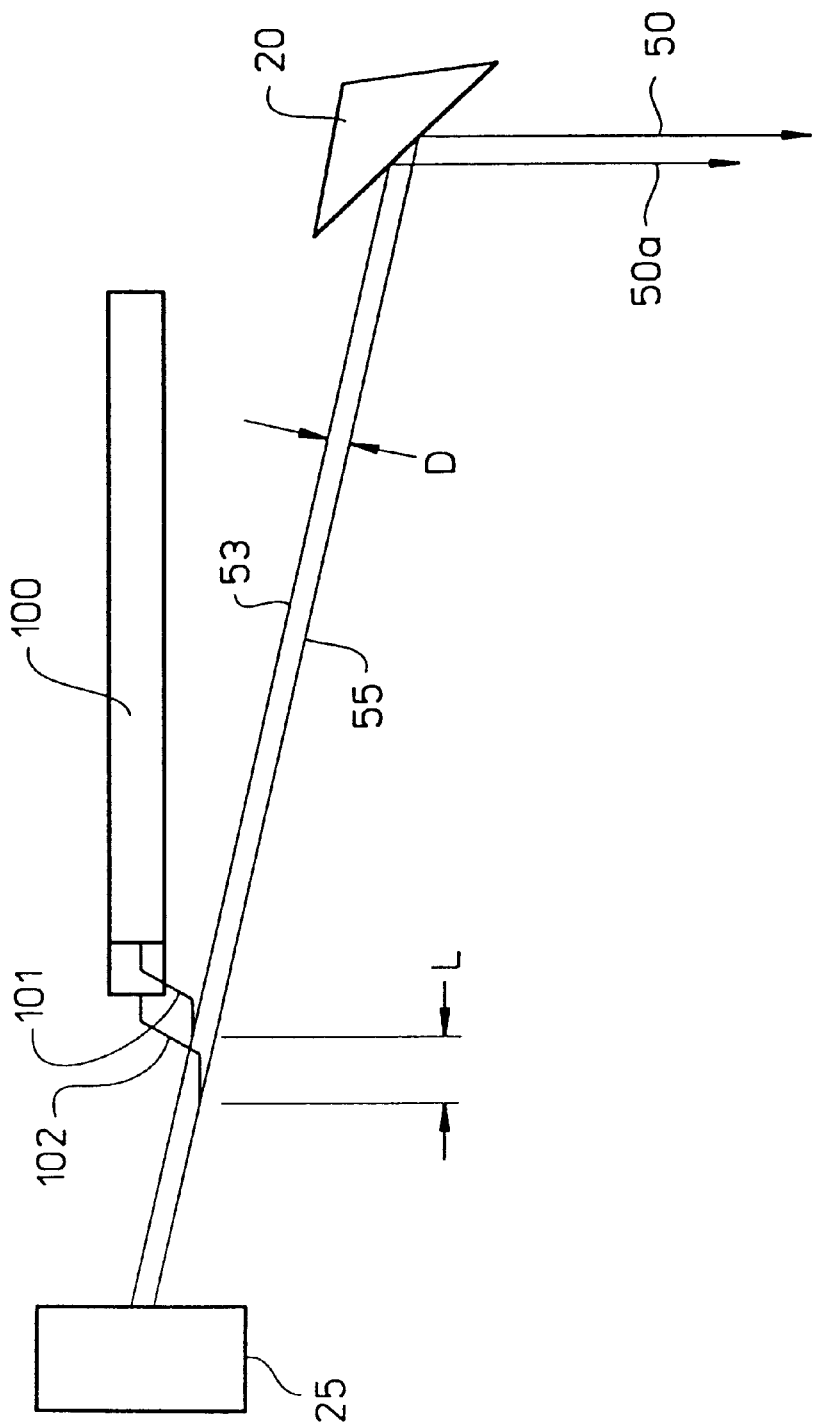
FIG. 5 is a schematic view to an enlarged scale illustrating the imaging of part of the IC.

It should be noted that each of the reflectors 18, 19.20 21 views the leads 101 on the far side (i.e., the side edge remote from the corresponding reflector of the IC) hence forming a cross-looking geometry (see FIG. 5). As illustrated in FIGS. 4a and 4b, the reflector 20 reflects the silhouettes, created by light source from light source part 25A, of the IC leads 101A through the optical path 50 into the lens 23 and then into the video camera 24. Similarly, the optical path 51 is a cross looking geometry where reflector 21 reflects light of light source part 25B passing by the leads 101B into the lens 23 and the video camera 24 as a silhouette. If the IC consists of leads 101 on all its four sides, then all the four reflectors 18, 19, 20 and 21 will reflect their respective far side leads 101 into the lens 23 and the video camera 24. The viewing optical paths have a portion passing by the lead 101 inclining at a small oblique angle α with respect to the inspection datum 15. This oblique angle a further allows leads 101 above the IC 100 package bottom to be successfully imaged and measured. In practice, the oblique angle α is no more than 10 degrees.

To enable the inspection system 10 to perform 3D inspection while the IC 100 is moving, the inspection system is adapted to cope with variations in positional shift when the image is acquired. The effect of the positional shift is illustrated in FIG. 5. The variation in the lateral position is labelled L, which will cause a deviation of the optical path from 50 to 50a. The deviation D of the optical path if not compensated will cause an error in the Z measurement, which is related to the coplanarity of the IC 100. To cope with this variation, the system 10 includes compensation means. The compensation means is described below with reference to FIG. 6, using reflectors 19 and 20 as an example, which are capable of imaging the orthogonal views of the leads 101.

As shown in FIG. 5, the optical path for viewing the corner lead 101 of the IC 100 is 52 for which the Y (the dimension into the page in FIG. 5) and Z (the dimension on the plane of FIG. 5 perpendicular to the Y axis and normal to the plane of the IC) co-ordinates can be measured. The corner lead 101 is located on the far side of the reflector 20. The reflector 20 views the corner lead 101 by optical path 53 for which the lateral position (regarding the X dimension) can be measured. Hence, by combining two adjacent pairs of reflected images, the X, Y, Z co-ordinates of a lead can be determined. For example, in FIG. 5, lead position 101 and lead position102 are the positions of the same lead 101 in two adjacent images when the light source 25 and the reflector 20 are moved relative to the IC 100. Thus with only one light source and one reflector, the X, Y, Z positions of the lead 101 can be determined. Therefore, using this technique of cross-looking geometry, one is able to obtain three dimensional information on a part (e.g., leads of an IC) with only one light source and only one camera.

Figure 6:
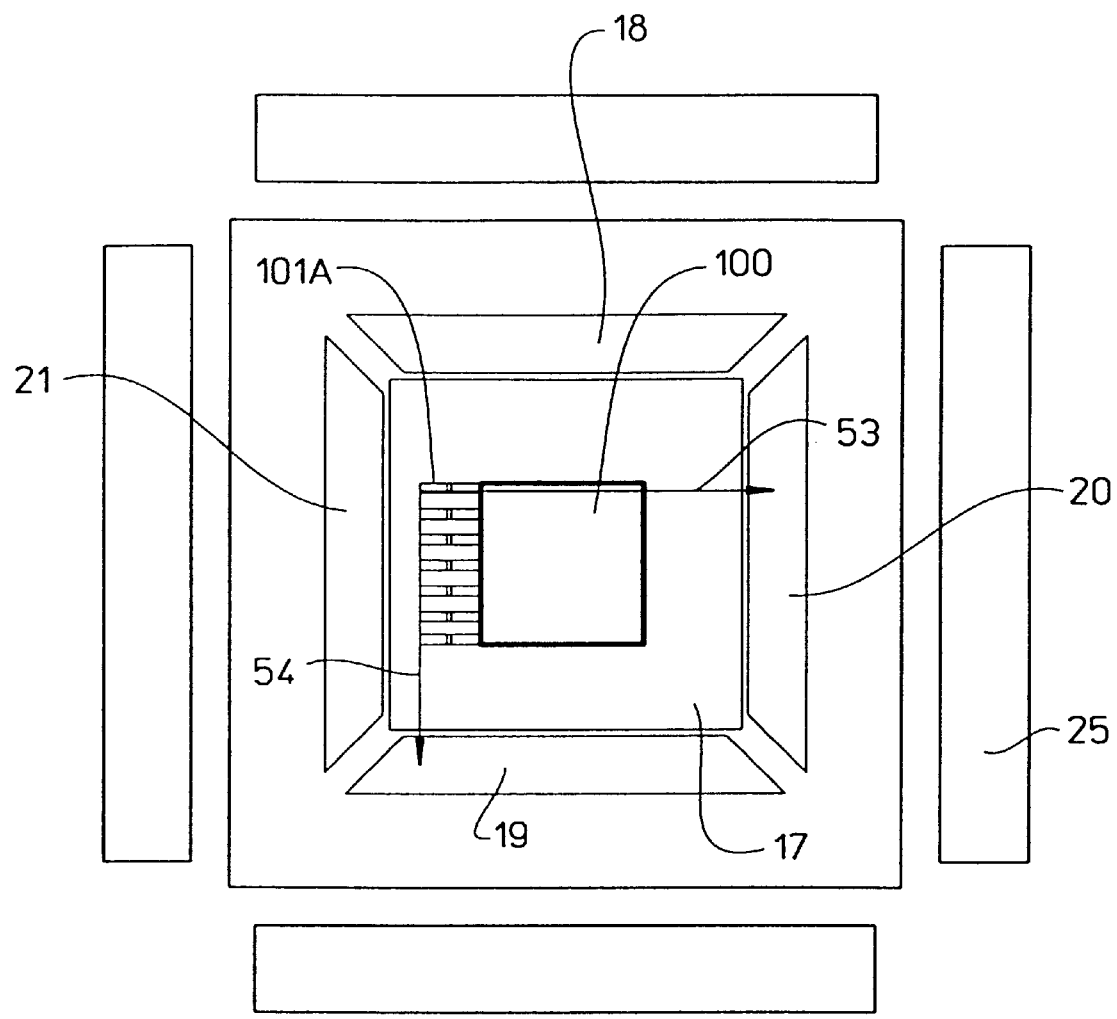
FIG. 6 is a plan view to an enlarged scale of the viewing optical module and IC in position.

FIG. 6 shows a bottom view at the window 17 with an IC 100 at its centre for imaging. Here, for illustrative clarity, leads are shown on only one side on the side edges of the IC 100. The lead 100A is imaged by light passing along light path 53 onto the reflector 20 and imaged by light passing along light path 54 onto the reflector 19. The light paths 53 and 54 are substantially about 90 degrees to each other. Here, for clarity, the silhouette images reflected by the reflectors 18, 19, 20, 21 are not shown in this figure. The underside of the IC 100 can also be seen if a light is present to illuminate it, for example, as described later relating to FIG. 10a.

Figure 7:
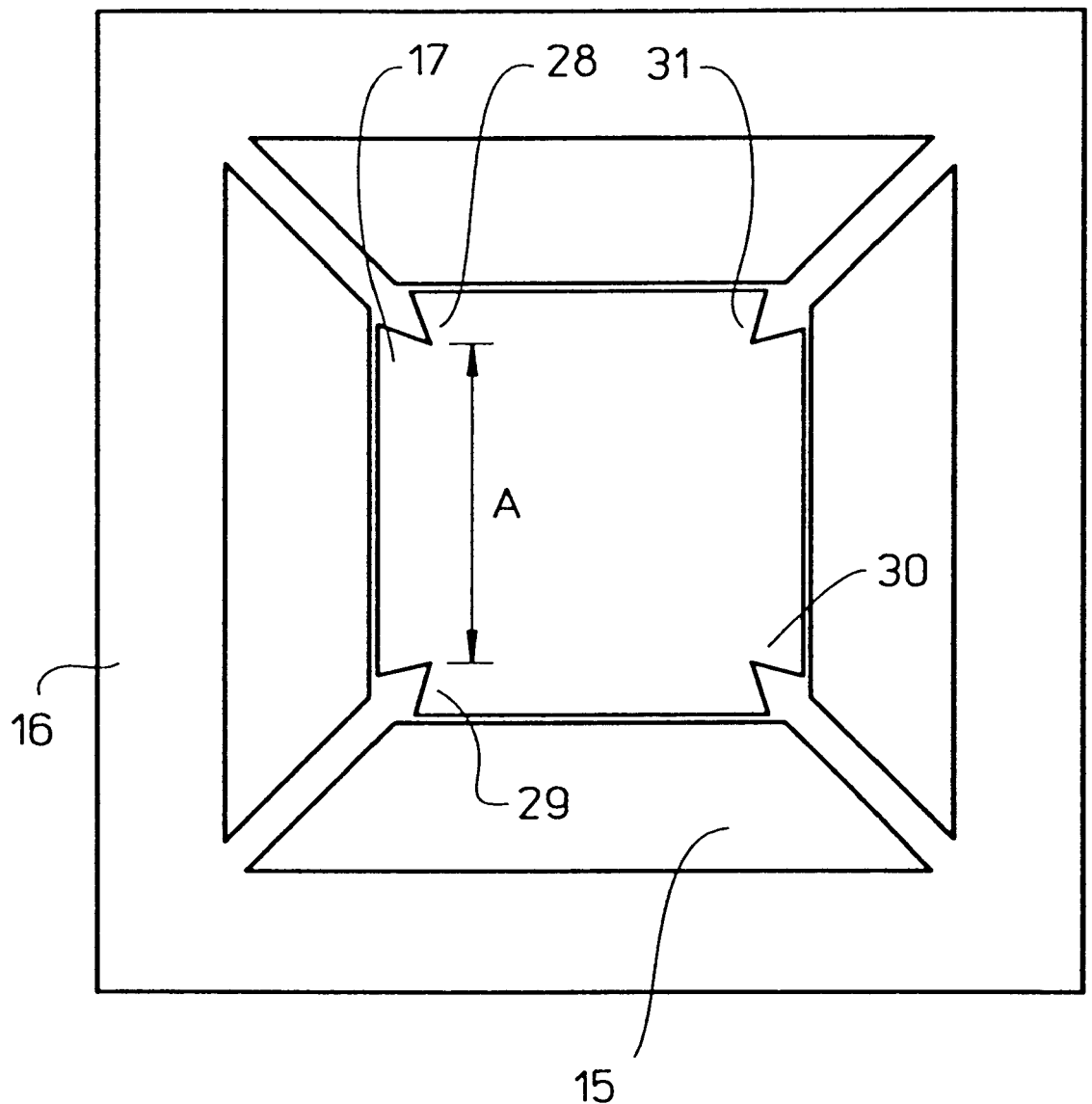
FIG. 7 is a plan view of a variation of the inspection datum of the viewing optical module.
Figure 8:
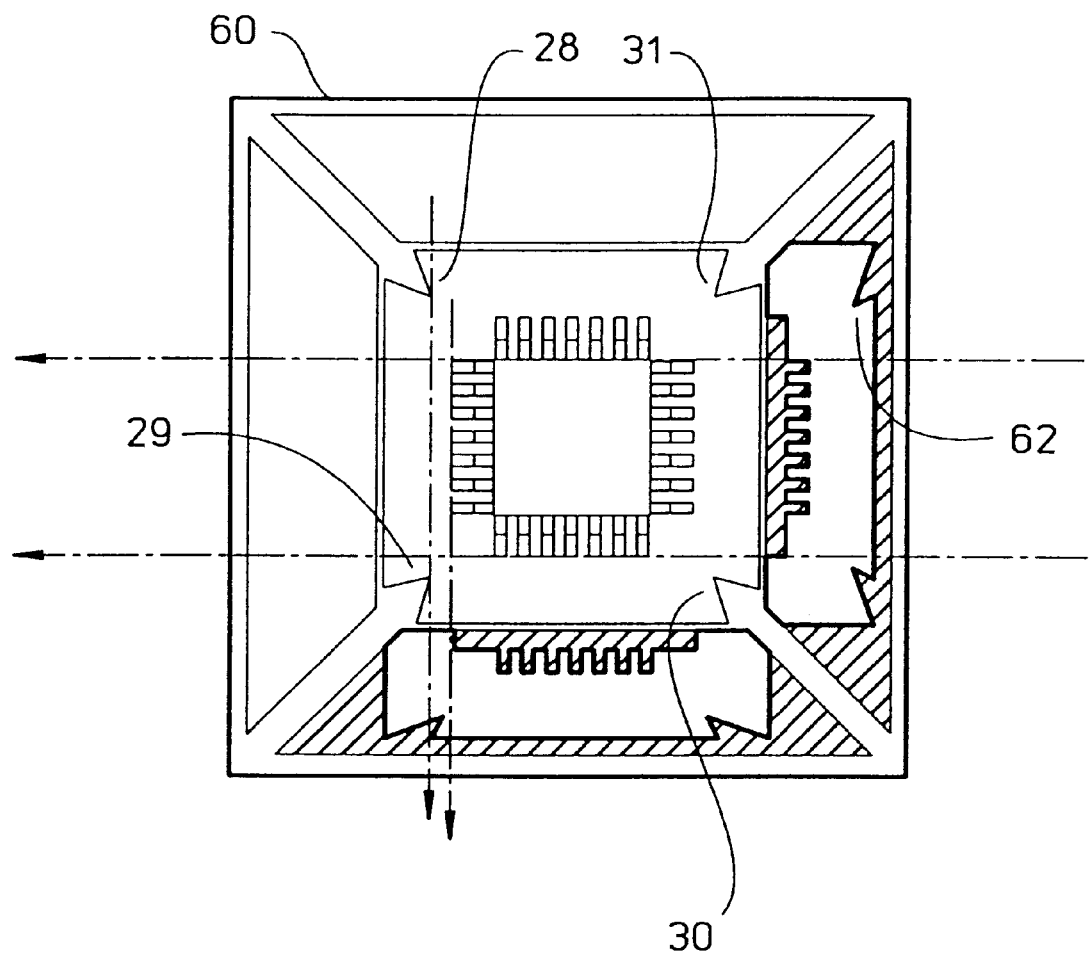
FIG. 8 is a schematic view illustrating the image generated from the viewing optical module.
Figure 9:
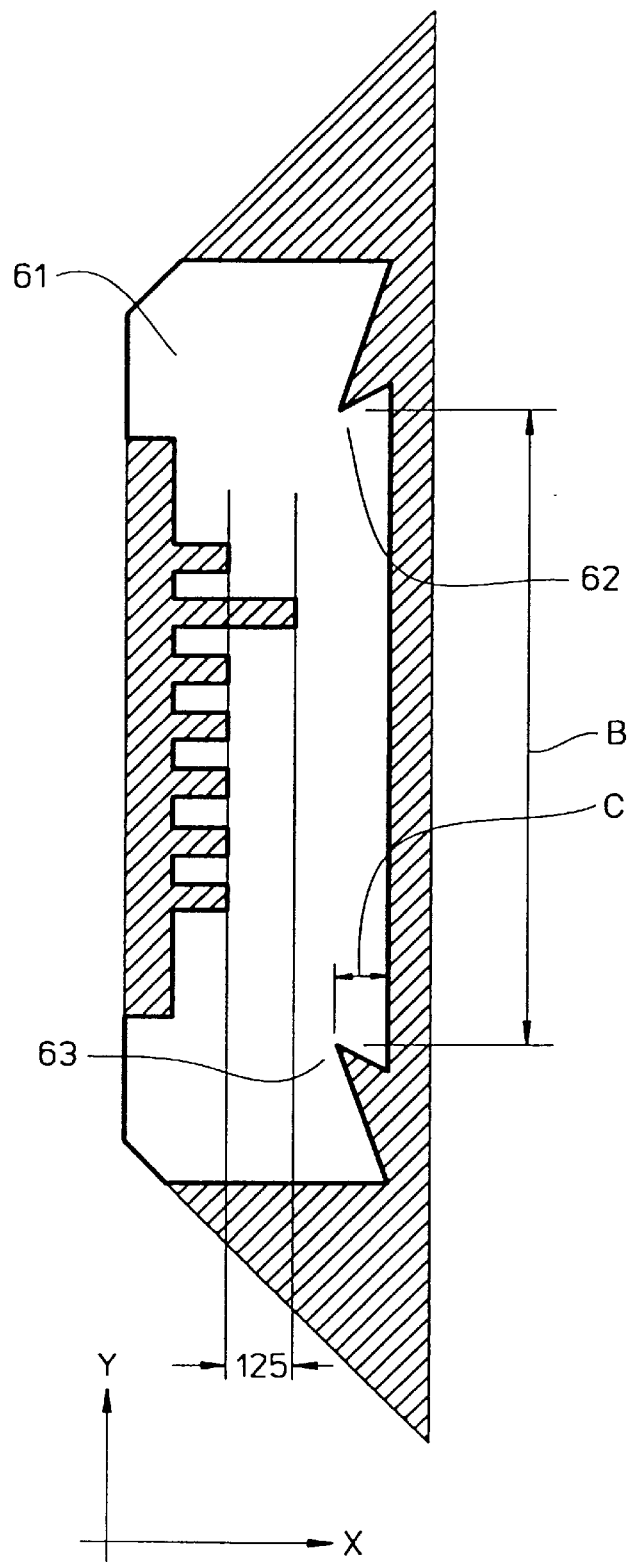
FIG. 9 is a detailed view of a part of the image of FIG. 8.

To facilitate calibration of the inspection system, the frame 16 may include reference points as illustrated in the FIG. 7. In the illustrated form, the dynamic reference points 28, 29, 30, 31 are distributed on the four corners of the viewing window 17. The four dynamic reference points 28, 29, 30, 31 form a known precise reference plane. The distance between any two of these dynamic reference points are precisely known and are pre-stored in the central processing module 13. The dynamic reference points and the inspection datum 15 are preferably machined out from a single piece of rigid material so that high precision and flatness can be maintained. For the purpose of describing the calibration procedure, reference is made to FIGS. 8 and 9. FIG. 8 shows an image 60 acquired by the camera 24 i.e., as seen from a position under the IC, whereas FIG. 9 is a part of this image showing specifically the image 61 reflecting from the reflector 20, through the lens 23 and onto the video camera 24. As can be seen, the dynamic reference point 28 is imaged onto point 62, whereas the dynamic point 29 is imaged onto point 63. The physical distance between the two dynamic reference points 28 and 29 is of a known value, A (see FIG. 7). As shown in FIG. 9, the distance (B) between imaged dynamic reference points 62 and 63 is measured in terms of pixels, which is a common term to denote the picture element in an digital array representing an image. Hence it becomes possible to calibrate the Y dimensional scale of this part of the image 61, which is reflected by reflector 20. The Y scale is equal to A/B. If A is measured in mm, then the unit for Y scale is mm per pixel. Similarly, the Y scale of this part of the image can be obtained by measuring the distance C, corresponding to how far the dynamic reference 63 extending out from the edge of the frame 16, in terms of pixel. The calibration procedure that has been described is equally applicable to all other three reflected sub images through reflectors 18, 19 and 21. Therefore, using the apparatus of the present invention, one is able to obtain distances in absolute units (e.g., mm, micron) between points in the object in different co-ordinates.

The image acquisition module 12 consists of a frame grabber (not shown in the figures) which receives the video signal from the video camera 24 and converts it into digital format which is known as a digital image corresponding to image 60 (see FIG. 8). It is also common in the art that the video camera 24 may output digital format video signal. The frame grabber further transmits the digital image 60 for digital image processing and analysis to be carried out by the central processing module 13. A sensor may be used to sense the position of the IC 100 when it is moved across the inspection datum 15 (see arrow R in FIG. 3) and triggers the image acquisition module 12 to acquire the image of the IC 100 when it is at an appropriate location above the viewing window 17. The trigger signal may also be derived from a motion controller of the pickup head 27 (see FIG. 3). The motion controller of the pickup head 27 may have an encoder that monitors the position of the pickup head 27 and hence the location of the IC 100. It is also contemplated that the motion controller can be part of the central processing module 13 as well.

The central processing module 13 processes the digital image 60 received from the image acquisition module 11. A task of the central processing module 13 is to compute the required parameters of the central processing module 13 will search and locate the positions of all leads 101 in the digital image 60. It will also detect the positions of all the dynamic reference points 27, 28, 29 and 30. Using two adjacent pair of reflected sub-images, it further determines the lateral position regarding the X dimension of the IC 100. The compensation factors which involve X scale and Y scale are then computed. Using the compensation factors, the central processing module 13 computes the X, Y, Z co-ordinates of all the leads; apply the compensation factors and calculate the required parameters of the IC 100 such as coplanarity, pitch, terminal dimension and others.

One of the important functions of the control module 14 is to sense the position of the IC 100 so that it can trigger the image acquisition module 12 to acquire the image. The control module further provides signals to control the movement of the light source platform 26. If required when the IC 100 is moving into the inspection datum, the control module will activate the light source platform to move down so as to provide a clear passage for the pickup head 27 with the IC 100. Once the IC 100 has moved into the inspection datum, the control module 14 will signal the light source platform 26 to move up to illuminate the leads 101. Once the IC is directly above the viewing window 17, the control module will signal the image acquisition module 12 to capture the image. Once the image or images of the IC 100 have been captured, the control module 14 will signal the light source platform to lower itself which again will provide a clear passage for the IC 100 to be moved out of the inspection datum.

Figure 10A:
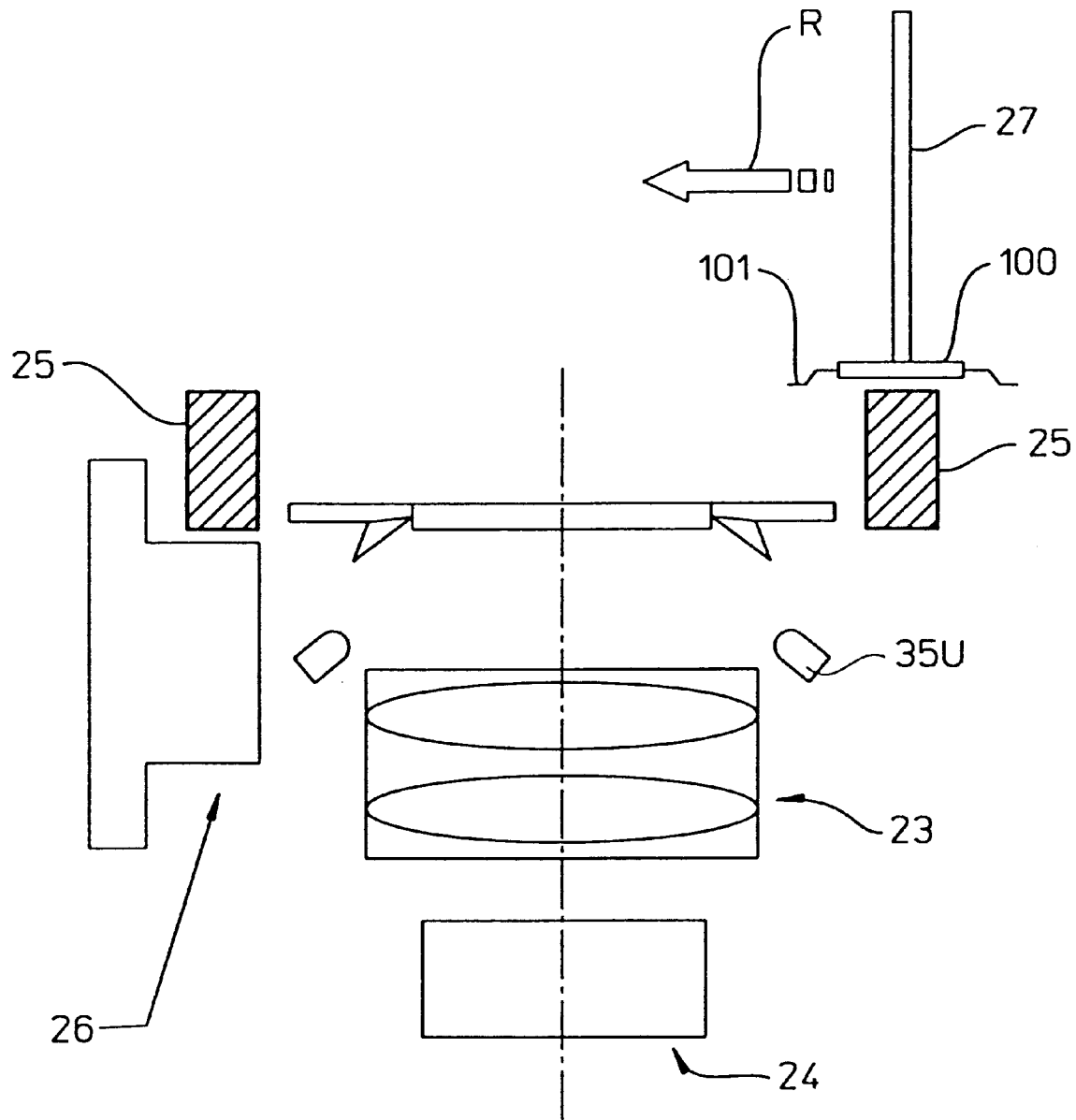
FIG. 10a is a side schematic view of another embodiment of the viewing optical module.

To provide additional imaging from another angle, in another embodiment, a light can be included to illuminate the leads from a direction at a substantial angle to the light originating from the light source 25. Preferably, to provide good reference for three-dimensional determination, the angle between light incident on or passing by closely a specific location by the two light sources is between 45 degree to 135 degree. An example would be to use a second light source to illuminate the leads from an angle about 90 degree to the light from the light source 25. FIG. 10a shows an embodiment of such an apparatus. In this embodiment, the light source 35U illuminates the IC 100 from the underside with front-lighting, so that the image when seen by the camera 24 can show the defects even on the surface of the leads or the underside surface of the IC. The light source 35U can have about a square shape similar to the light souse 25 to provide an even illumination on the leads and the underside of the IC 100. Using this technique of using two light source, for example, with two light sources illuminating the IC leads so that light from the two sources illuminate the same lead at a substantial angle to one another, a defect on a lead or a portion of a lead that is bent and twisted in just the right way as to be difficult to detect using one light source can be easily detected using the other. Illumining the underside of the object with front-light, details (e.g., defects on the IC package) not previously observable can be seen. This provide an additional safeguard against allowing a defective product to pass without noticing the defect Furthermore, a second light source provides a second image, which allows three dimensional information to be determined with only one picture of image received by the camera. In other words, in the same image received by the camera, observation is made from two different angles, thereby being able to see variations from standard in all three dimensions X, Y, and X even without moving the object between two imaging steps.

Figure 10B:
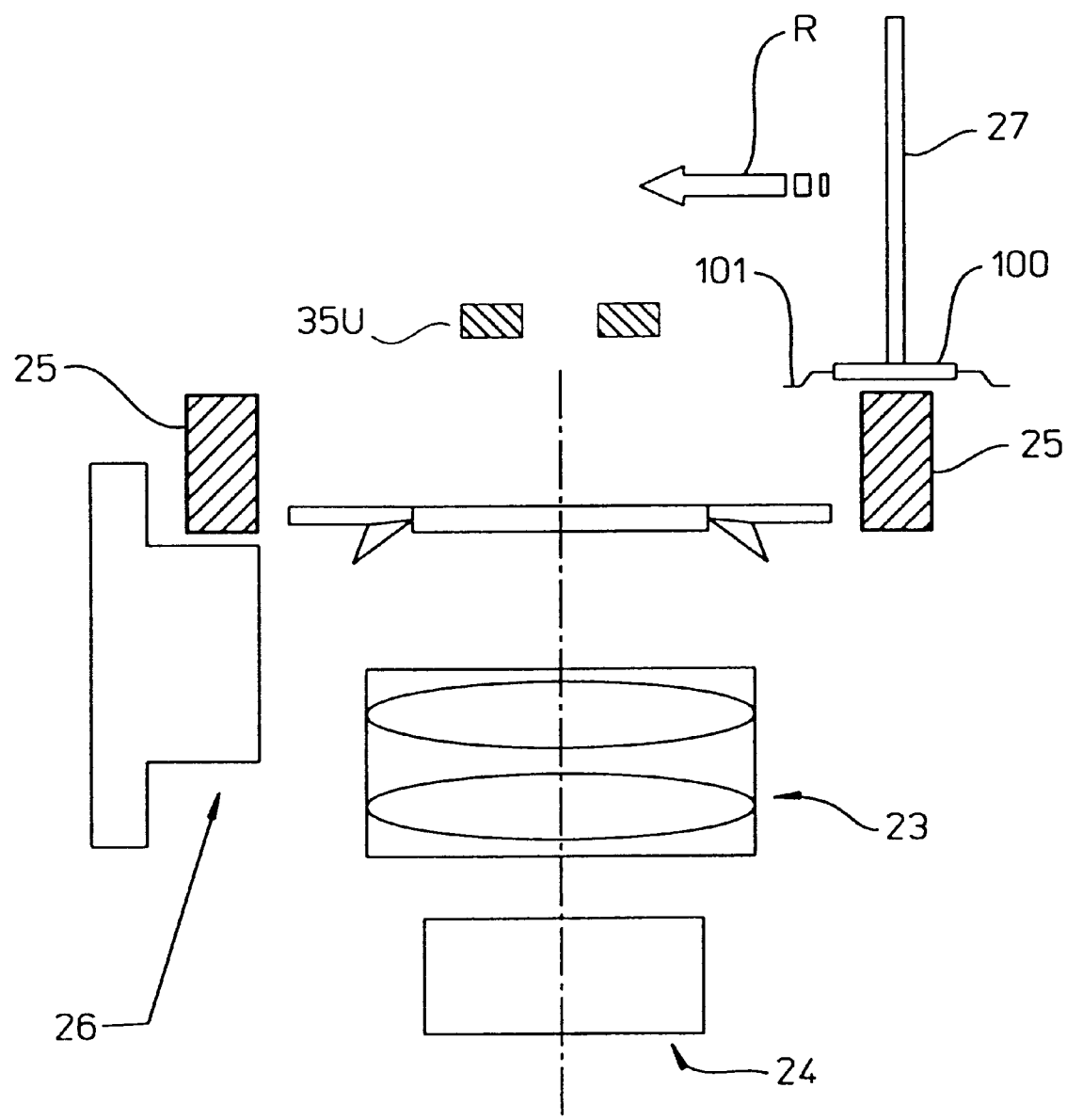
FIG. 10b is a side schematic view of yet another embodiment of the viewing optical module.
Figure 11A:
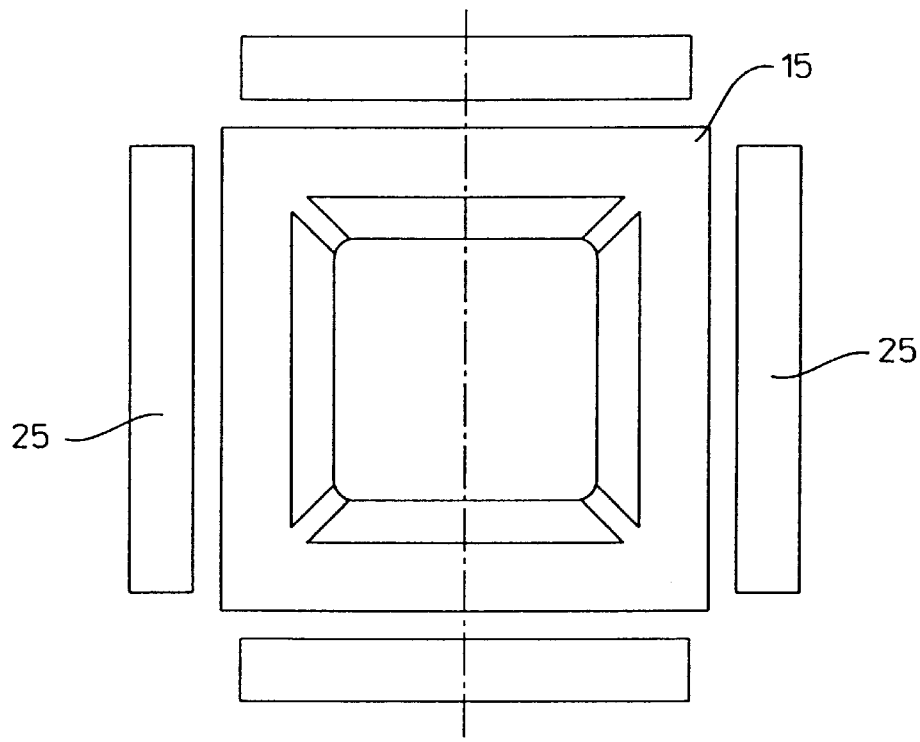
FIGS. 11a and 11b are a plan schematic view and a cross-sectional schematic elevation respectively of an alternative embodiment of the viewing optical module.
Figure 11B:
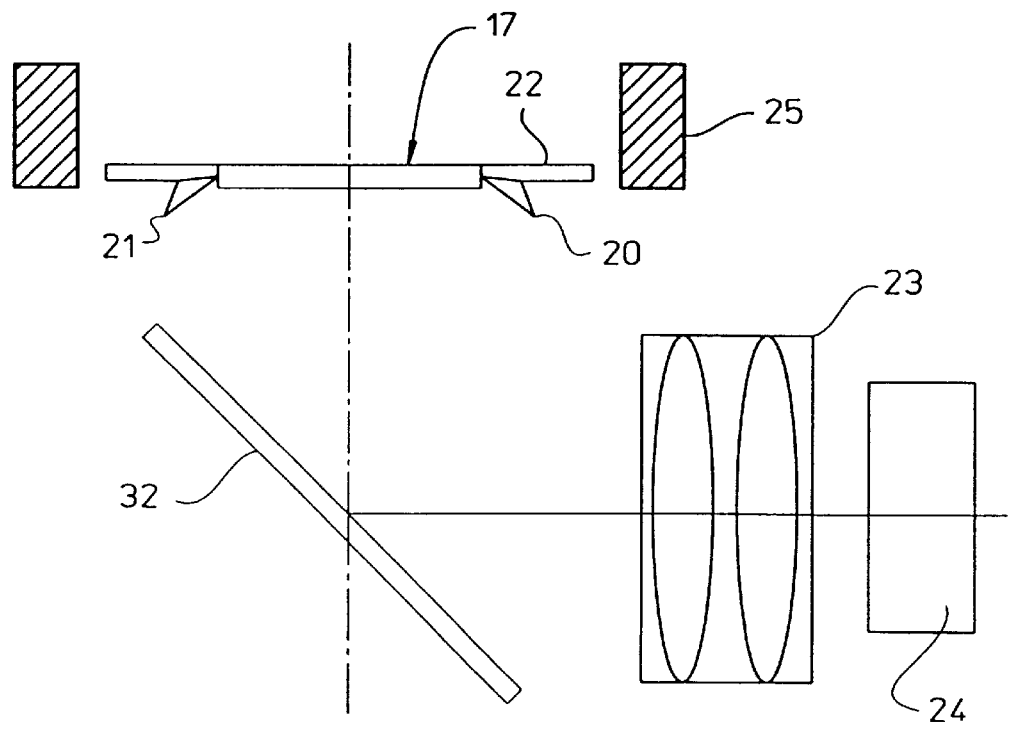

In another embodiment of using two light sources emitting light at an angle to the same area, shown in FIG. 10b, a second light source 35V above the IC 100 in additional to light source 25 can be used to provide the illumination at an substantial angle relative to the light from light source 25. In this case, in a back-lighting technique, the IC 100 interposes between the second light source 35V and the camera 24 such that the light passes the leads 101 of the IC to the camera to form a silhouette type of image. Preferably, the light source 35V have portions that can be moved out of the way to allow the IC 100 and the pickup head 27 to pass before and after imaging. Also, if preferred, but not required, the two light sources can be turned on at a different time so that they will not interfere with each other. As used herein, as long as light from the different light sources impinge on the camera and are sensed simultaneously, such a sensing process by the camera is considered to be one imaging herein and the image sensed, although having information derived from different light sources, is considered to be a single temporal image.

In yet another embodiment, if preferred, all three kinds of light sources shown in FIG. 10a and FIG. 10 can be used.

There are many other variations to the specific embodiments of the present invention. For example, as illustrated in FIGS. 10a and 10b, it is possible to include a mirror 32 to redirect the light by 90 degree so that the lens 23 and the video cameras 24 can be aligned horizontally rather than vertically. In this case, in the present disclosure, the optical axis of the camera 24 is still considered to pass through the plane of the IC 100 in the window.

This example illustrates the possibility of changing the physical layout of the present invention.

The invention has been designed with consideration of, but not exclusively, for the inspection of integrated circuit leads and embodiments of the invention herein have been described in that context. However, it is to be appreciated that the invention has broader applications and is not limited to that particular use. It will be appreciated that various modifications and improvements as well as additions can be made to the parts hereinafter before described without departing from the spirit or ambit of the present invention.

What is claimed is:

1. An apparatus for inspecting an object having a plane, comprising:

a camera for sensing an image of the object, the camera having an optical axis passing through the object normal to the plane of the object;

an oblique light source for radiating light on the object obliquely to the plane of the object, the oblique light source having a portion positioned on one side of the optical axis;

a reflector positioned on the opposite side of the optical axis relative to the portion of the oblique light source for reflecting light that crosses the optical axis from the oblique light source to the camera, such that a portion of the object interposes between the portion of the oblique light source and the reflector to Image the shape of that object portion on the camera; and a planar datum having a window through which light from the oblique light source passes obliquely to the reflector, the planar datum blocking light from directly passing from the light source to the camera without reflecting by the reflector during imaging.

2. An apparatus according to claim 1, wherein the object is an integrated circuit, the apparatus comprises at least one reflector substantially surrounding the integrated circuit about the optical axis, and the oblique light source substantially surrounds the integrated circuit about the optical axis, so as to radiate light as back light on all side edges of the integrated circuit about the optical axis to image on the camera by reflecting from the at least one reflector.

3. An apparatus according to claim 2 wherein the oblique light source radiates light on the side edges of the integrated circuit at an angle of 10 degrees or less to the plane of the integrated circuit, said light to be reflected by the reflectors to the camera.

4. An apparatus according to claim 1, wherein the reflector and the light source are movable relative to the object to obtain two or more different images of a same part of the object to obtain three dimensional information of that part of the object.

5. An apparatus according to claim 1, further comprising a second light source radiating light on a side edge of the object, wherein the light from the second light source then passes from the side edge of the object and reaches without crossing the optical axis an optical element for directing said light so as to be sensed by the camera.

6. An apparatus according to claim 4 wherein the second light source faces the object on the same side of the object as the camera to illuminate the object as a front-light.

7. An apparatus according to claim 4 wherein the second light source faces the object on the opposite side of the object as the camera to illuminate the object as a back-light.

8. An apparatus according to claim 5 wherein the second light source illuminates the object at a substantial angle to the light impinging on the reflectors from the oblique light source.

9. An apparatus according to claim 1 wherein the oblique light source is positioned on a side of the datum distal to the camera and the reflector is positioned on the same side of the datum as the camera.

10. An apparatus according to claim 1 wherein the object is a generally rectangular integrated circuit having leads extending from two opposite side edges, and light emitted from the oblique light source passes the leads to reach the reflector whereby a silhouette image of the leads is reflected to the camera.

11. An apparatus according to claim 1, further comprising a processor for processing signals from the camera to determine the contour of the side edge of the integrated circuit in order to determine the quality thereof.

12. A method of inspecting the quality of an integrated circuit having a plane, comprising sensing an image of the integrated circuit along an optical axis which faces the integrated circuit and passes through the integrated circuit in a direction normal to the integrated circuit plane;

directing light past a portion of the integrated circuit in an oblique direction relative to the integrated circuit plane for reflection at a position on the opposite side of the optical axis;

reflecting the light passing from the portion of the integrated circuit to image the shape of the portion, the shape indicating the quality of the integrated circuit; and employing a planar datum, the datum having a window through which the obliquely directed light passes to the reflection position, the planar datum blocking the obliquely directed light from being imaged without reflecting.

13. A method according to claim 12, further comprising emitting light from a first light source which substantially surrounds the integrated circuit about the optical axis in a direction oblique to the integrated circuit plane for reflection on at least four sides substantially surrounding the integrated circuit about the optical axis, so as to radiate light as back-light on all side edges of the integrated circuit about the optical axis to image by reflection.

14. A method according to claim 13, further comprising directing light from a second light source so as to radiate a side edge of the integrated circuit, wherein the radiated light passes from the side edge and reaches an optical element without crossing the optical axis; and using the optical element to direct the light which passes from the side edge for imaging.

15. A method according to claim 14, wherein the light from the second light source illuminates the integrated circuit as front-lighting.

16. A method according to claim 14, wherein the light from the second light source is directed at a substantial angle to the obliquely directed light.

17. A method of inspecting the quality of an integrated circuit having a plane and a plurality of side edges, comprising:

sensing an image of the Integrated circuit along an optical axis which faces the integrated circuit and which passes through the integrated circuit in a direction normal to the integrated circuit plane;

emitting light from a light source which substantially surrounds the integrated circuit about the optical axis such that light is directed past all side edges of the integrated circuit In an oblique direction relative to the integrated circuit plane, for reflection on the opposite side of the optical axis such that the emitted light acts as back-lighting on all the side edges; and reflecting the light passing from the edges of the integrated circuit on at least four sides substantially surrounding the integrated circuit about the optical axis, to image the shape of the portion, the shape indicating the quality of the integrated circuit.

* * * * *

UNITED STATES PATENT AND TRADEMARK OFFICE
CERTIFICATE OF CORRECTION

PATENT NO. : 6,055,055
DATED : April 25, 2000
INVENTOR(S) : Peng Seng Toh

It is certified that error appears in the above-identified patent and that said Letters Patent is hereby corrected as shown below:

<u>Column 9,</u>
Line 37, "claim 4", should read -- claim 5 --.
Line 40, "claim 4", should read -- claim 5 --.

Signed and Sealed this

Thirty-first Day of July, 2001

*Attest:*

*Nicholas P. Godici*

*Attesting Officer*

NICHOLAS P. GODICI
*Acting Director of the United States Patent and Trademark Office*